(12) United States Patent
Takano (10) Patent No.: US 10,504,356 B2
(45) Date of Patent: Dec. 10, 2019

(54) INFORMATION COMMUNICATION TERMINAL

(71) Applicant: OMRON HEALTHCARE CO., LTD., Kyoto (JP)

(72) Inventor: Yuki Takano, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 0 days.

(21) Appl. No.: 16/029,700

(22) Filed: Jul. 9, 2018

(65) Prior Publication Data

US 2018/0315294 A1 Nov. 1, 2018

Related U.S. Application Data

(63) Continuation of application No. PCT/JP2016/082847, filed on Nov. 4, 2016.

(30) Foreign Application Priority Data

Jan. 18, 2016 (JP) .................. 2016-007173

(51) Int. Cl.
*G08B 25/00* (2006.01)
*A61B 5/00* (2006.01)

(52) U.S. Cl.
CPC .......... *G08B 25/001* (2013.01); *A61B 5/4809* (2013.01); *A61B 5/0022* (2013.01); *A61B 5/4812* (2013.01)

(58) Field of Classification Search
None
See application file for complete search history.

(56) References Cited

U.S. PATENT DOCUMENTS

| 9,306,899 B1* | 4/2016 | Vendrow ................. H04L 51/34 |
| 2005/0101302 A1* | 5/2005 | Vogedes ............ H04M 1/72522 |
| | | 455/412.2 |
| 2015/0119667 A1* | 4/2015 | Reihman .............. A61B 5/6802 |
| | | 600/365 |
| 2016/0029899 A1* | 2/2016 | Kim ................... A61B 5/02438 |
| | | 455/414.1 |

FOREIGN PATENT DOCUMENTS

| JP | 2007241503 A | 9/2007 |
| JP | 2014006595 A | 1/2014 |

OTHER PUBLICATIONS

International Search Report dated Dec. 20, 2016 of corresponding application No. PCT/JP2016/082847; 1 pg.

* cited by examiner

*Primary Examiner* — John F Mortell

(74) *Attorney, Agent, or Firm* — Maier & Maier, PLLC (57) ABSTRACT

An information communication terminal includes: a sleeping state determination unit configured to determine a sleeping state of a user; a reception unit configured to receive information transmitted to the user from a terminal of a sender; and a notification unit configured to notify the user that the information has been received by the reception unit. The reception unit receives the information and an importance level set for the information by the sender, and the notification unit changes a method for performing notification based on the importance level set for the information and the sleeping state of the user determined by the sleeping state determination unit.

8 Claims, 5 Drawing Sheets

| IMPORTANCE LEVEL | SLEEPING STATE | METHOD FOR PERFORMING NOTIFICATION |
|---|---|---|
| LEVEL 0 | NOT ASLEEP | PERFORM NOTIFICATION |
| | ASLEEP | DO NOT PERFORM NOTIFICATION |
| LEVEL 1 | NOT ASLEEP | PERFORM NOTIFICATION |
| | IN LIGHT SLEEP | PERFORM NOTIFICATION |
| | IN DEEP SLEEP | DO NOT PERFORM NOTIFICATION |
| LEVEL 2 | NOT ASLEEP | PERFORM NOTIFICATION |
| | ASLEEP | PERFORM NOTIFICATION |
| LEVEL 3 | NOT ASLEEP | PERFORM NOTIFICATION |
| | ASLEEP | PERFORM NOTIFICATION UNTIL RECIPIENT WAKES UP |

FIG. 5

| IMPORTANCE LEVEL | SLEEPING STATE | METHOD FOR PERFORMING NOTIFICATION |
|---|---|---|
| LEVEL 0 | NOT ASLEEP | PERFORM NOTIFICATION USING VIBRATION |
| | ASLEEP | DO NOT PERFORM NOTIFICATION |
| LEVEL 1 | NOT ASLEEP | PERFORM NOTIFICATION USING VIBRATION |
| | IN LIGHT SLEEP | PERFORM NOTIFICATION USING VIBRATION |
| | IN DEEP SLEEP | DO NOT PERFORM NOTIFICATION |
| LEVEL 2 | NOT ASLEEP | PERFORM NOTIFICATION USING VIBRATION AND SOUND |
| | IN LIGHT SLEEP | PERFORM NOTIFICATION USING VIBRATION AND SOUND |
| | IN DEEP SLEEP | DO NOT PERFORM NOTIFICATION |
| LEVEL 3 | NOT ASLEEP | PERFORM NOTIFICATION USING VIBRATION |
| | ASLEEP | PERFORM NOTIFICATION USING VIBRATION |
| LEVEL 4 | NOT ASLEEP | PERFORM NOTIFICATION USING VIBRATION AND SOUND |
| | ASLEEP | PERFORM NOTIFICATION USING VIBRATION AND SOUND |
| LEVEL 5 | NOT ASLEEP | PERFORM NOTIFICATION USING VIBRATION AND SOUND |
| | ASLEEP | PERFORM NOTIFICATION USING VIBRATION AND SOUND UNTIL RECIPIENT WAKES UP |

FIG. 6

INFORMATION COMMUNICATION TERMINAL

BACKGROUND

Field

The present invention relates to a technique for notifying a user of reception of information.

Description of the Related Art

Due to the widespread use of information communication terminals such as mobile phones, smartphones, and wearable terminals, it has become possible to easily send information (e.g., e-mail messages, image data) at any time to a person at a remote location. The mechanism for this kind of information communication can realize communication with a partner (the recipient of the information) with no restriction on time or location, and thus is very convenient. However, since it is possible to unilaterally send information regardless of the state of the partner, it is also possible to cause the partner inconvenience in some cases. For example, it is common for this type of terminal to perform notification using sound, vibration, or the like when information is received, and if such notification is performed while the recipient is sleeping, the recipient's sleep will be disturbed. If the received information is not important (e.g., if it is information of low urgency, such as information that may be checked after waking up), the recipient may feel displeasure at the fact that his or her sleep was disturbed.

Conventionally, as a means for avoiding such an inconvenience, the recipient (user of the terminal) turns off the power of the terminal or sets it to a silent mode (a mode in which a notification sound and vibration are turned off) before sleeping. However, in the case of turning off the power or setting the terminal to the silent mode, notification is no longer performed, and therefore there is a problem in that the recipient cannot notice when important information is received.

In order to solve the above-described problem, it is sufficient to be able to realize information communication or notification control in which consideration is given to the sender's desire to let the recipient check the information tomorrow if the recipient is asleep, or to have the recipient check the information right away because it is important, and in which consideration is given to the state of the recipient, such as being asleep. However, such a mechanism has not conventionally existed.

Note that Japanese Patent Application Laid-open No. 2014-6595 discloses a method in which a notification apparatus in an earthquake notification system determines the sleeping state of the user and increases the volume of an earthquake notification the deeper the sleep of the user is and the larger the earthquake is. This method serves as a reference since the certainty with which the information is transmitted to the sleeping user is increased, but the above-described problem of transmitting information between individuals is not resolved.

SUMMARY

The present invention has been made in view of the foregoing circumstances and aims to provide a technique for enabling notification control in which consideration is given to the desire of the sender of information and to the state of the recipient of the information.

The present invention provides an information communication terminal according to the present invention is an information communication terminal including: a sleeping state determination unit configured to determine a sleeping state of a user; a reception unit configured to receive information transmitted to the user from a terminal of a sender; and a notification unit configured to notify the user that the information has been received by the reception unit, wherein the reception unit receives the information and an importance level set for the information by the sender, and the notification unit changes a method for performing notification based on the importance level set for the information and the sleeping state of the user determined by the sleeping state determination unit.

Here, "changing the method of performing notification" includes switching between performing and not performing notification, changing the strength of notification, changing the length of notification, changing the means of notification (sound, vibration, light, etc.), and the like. The "importance level" may be set to one of two levels, namely high and low, or may be set to one of three or more levels, namely levels 0 to N (N being an integer that is 2 or more). Note that if the importance level is not set for the received information, it is sufficient that a default importance level (e.g., the lowest importance level, a predetermined importance level, or the highest importance level) is regarded as having been set.

DETAILED DESCRIPTION

Preferred embodiments of the present invention will be described hereinafter with reference to the drawings. Note that the descriptions of the configurations described hereinafter are to be modified as appropriate according to the configuration and various conditions of the system to which the invention is applied, and the scope of the present invention is not limited to the following description.

<System Configuration>

Figure 1:
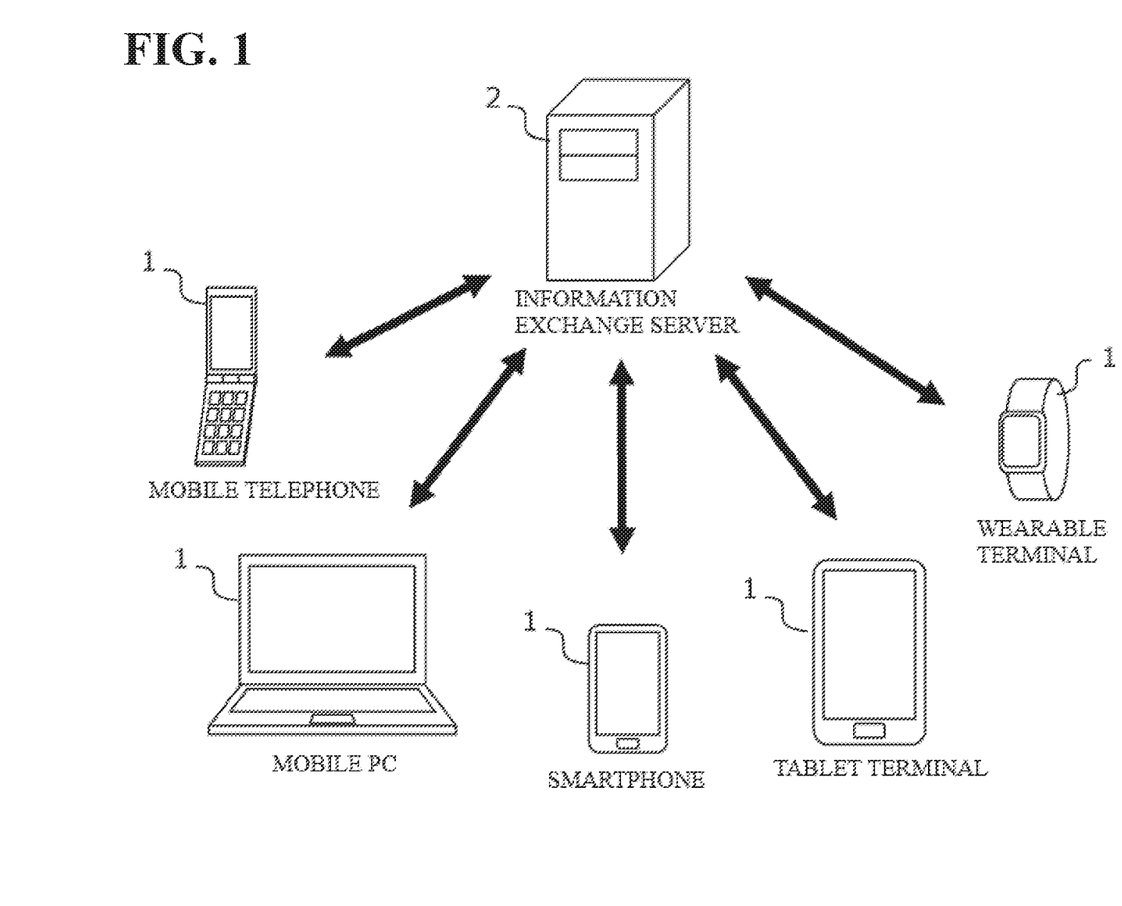
FIG. 1 is a diagram showing an overall configuration of an information communication system according to an embodiment of the present invention.

An overall configuration of an information communication system according to an embodiment of the present invention will be described hereinafter with reference to FIG. 1. The information communication system is a system for realizing exchange (transmission and reception) of information between users, and is constituted roughly by including multiple terminals 1 operated by the users, and an information exchange server 2 that provides a service of exchanging information between the terminals 1. The terminals 1 and the information exchange server 2 are connected by a wide area communication network such as the Internet. An information exchange service provided by the information exchange server 2 is typically e-mail transmission and reception, message transmission and reception, exchange of data such as images and videos (file exchange), or the like, but the present invention can be applied also to an information exchange service other than these.

<Information Exchange Server>

The information exchange server 2 is a computer system that mediates transmission and reception of information between the multiple terminals 1. As a basic hardware configuration, the information exchange server 2 includes a CPU (processor), a memory (storage apparatus), a storage (large-capacity storage apparatus), and a communication apparatus, and various types of later-described information processing are realized by the CPU executing a program stored in the memory. In order to guarantee robustness, the information exchange server 2 may be constituted by multiple computers or may use distributed computing or cloud computing.

<Terminal>

The terminal 1 is a device held and operated by a user. Any type of terminal may be used, as long as it is an information communication terminal that has a wireless communication (Wi-Fi, Bluetooth (registered trademark), mobile phone communication, etc.) function, and for example, a mobile phone (feature phone), a smartphone, a tablet terminal, a mobile personal computer, a wearable terminal, and the like are representative examples thereof.

As a basic hardware configuration, every type of terminal 1 includes a CPU (processor), a memory (storage apparatus), an input apparatus, a display apparatus, a notification apparatus, and a wireless communication apparatus, and various types of later-described information processing are realized by the CPU executing a program stored in the memory. The input apparatus is, for example, a keyboard, a pointing device, a touch pad, a touch panel display also serving as a display apparatus, or the like. The notification apparatus is a device that notifies the user of the occurrence of some event through a means such as sound, light, or vibrations, and for example, a speaker, an LED lamp, a vibrator, a display, or the like is used thereas. In the present embodiment, an example will be described in which notification of the occurrence of an event, namely reception of information from another terminal, is performed.

Figure 2:
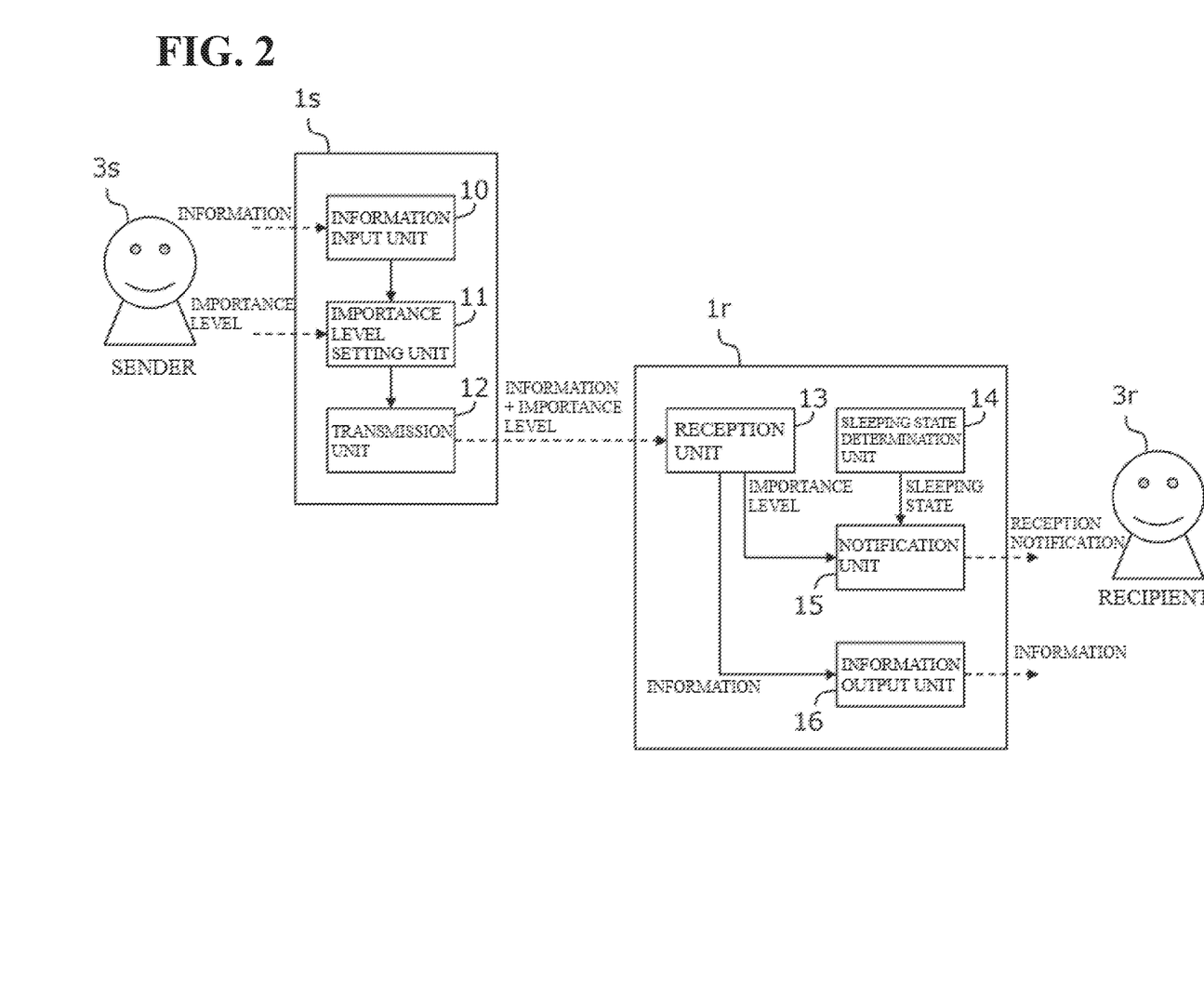
FIG. 2 is a diagram showing a functional configuration of a transmitting terminal and a receiving terminal.

FIG. 2 shows a configuration of functions relating to information exchange among the functions of the terminal 1. These functions can be used by installing, in the terminal 1, an information exchange application program (hereinafter referred to simply as an "information exchange application") that can be obtained from the information exchange server 2 or another application server. In order to make it easier to understand the description, FIG. 2 illustrates a configuration of functions relating to information transmission in the terminal (indicated by reference numeral 1s) of the sender 3s of the information and a configuration of functions relating to information reception in the terminal (indicated by reference numeral 1r) of the recipient 3r of the information. However, in actuality, a terminal 1 in which the information exchange application is installed includes the functions for both information transmission and information reception.

As functions relating to information transmission, the transmitting terminal 1s includes an information input unit 10, an importance level setting unit 11, and a transmission unit 12. The information input unit 10 is a function that allows the sender 3s to input the information to be transmitted to the recipient 3r, and for example, provides a user interface for inputting an address, a title, and a message for e-mail, a user interface for creating or designating data to be transmitted, or the like. The importance level setting unit 11 is a function that allows the sender 3s to set the "information importance level" to be added to the information to be transmitted. The details of the information importance level will be described later. The transmission unit 12 is a function that transmits the information to which the importance level was added to the receiving terminal 1r via the information exchange server 2.

As functions relating to information reception, the receiving terminal 1r has a reception unit 13, a sleeping state determination unit 14, a notification unit 15, and an information output unit 16. The reception unit 13 is a function that receives the information transmitted from the transmitting terminal 1s via the information exchange server 2. The sleeping state determination unit 14 is a function that determines the sleeping state of the recipient 3r. The details of the determination of the sleeping state will be described later. The notification unit 15 is a function that notifies the recipient 3r that the information was received. The details of the notification control performed by the notification unit 15 will be described later. The information output unit 16 is a function that displays the received information.

<Information Importance Level>

With the information exchange service of the present embodiment, the sender 3s can set the "importance level" for the information to be sent by the sender 3s. The importance level set by the sender 3s is used for notification control in the receiving terminal 1r. Note that the importance level may be set as one of two levels, namely high or low, or may be set as one of three or more levels, namely levels 0 to N (N being an integer that is 2 or more).

Figure 3:
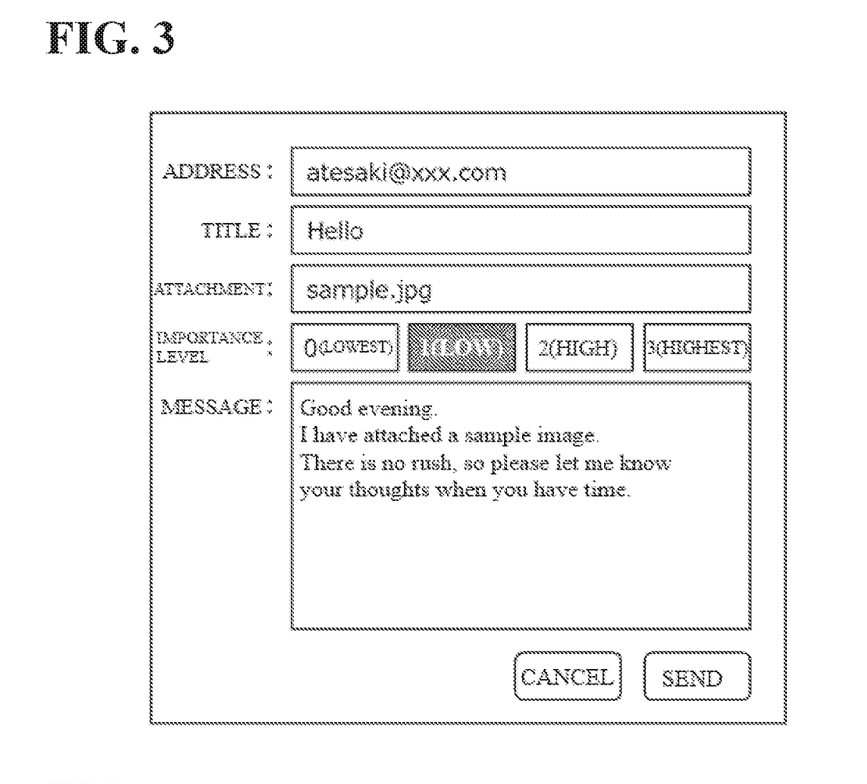
FIG. 3 is a diagram showing an example of a user interface for inputting information and setting an importance level.

FIG. 3 shows an example of a user interface provided by the information input unit 10 of the transmitting terminal 1s. This user interface is an example for e-mail transmission, and it is possible to input an address (address of the recipient 3r), a title, a message, an attached file, an importance level, and the like of the e-mail. The importance level can be selected from among four levels, namely 0 (lowest), 1 (low), 2 (high), and 3 (highest). The importance level set by the sender 3s is sent attached to information (the e-mail in the example in FIG. 3). For example, in the case of general electronic mail on the Internet, the information regarding the importance level need only be described in the mail header (in this case, an existing header field such as X-priority may be used).

<Determination of Sleeping State>

The sleeping state determination unit 14 determines the sleeping state of the recipient 3r (i.e., the user of the receiving terminal 1r). There is no limitation on the method or means for sleep detection and sleeping state determination. For example, the sleeping state determination unit 14 may measure the bodily movement of the user using a bodily movement sensor such as an acceleration sensor and determine (estimate) the sleeping state based on whether or not there is bodily movement and the size of the bodily movement. Alternatively, the sleeping state determination unit 14 may determine (estimate) the sleeping state based on the heart rate, fluctuations in the heart rate, or the like measured by a sensor such as a heart rate meter, a pulse meter, or a blood pressure monitor. Alternatively, the sleeping state determination unit 14 may determine (estimate) the sleeping state based on body temperature, fluctuations in the body temperature, or the like measured by a sensor such as a thermometer or an infrared sensor. Alternatively, the sleeping state determination unit 14 may determine (estimate) the sleeping state based on bodily movement, facial expression (state of eyelids), or the like of the user measured using an image sensor such as a camera. The result of the determination of the sleeping state can be obtained as one of two values indicating being asleep and not being asleep, or can be obtained as one of multiple values indicating deep sleep, light sleep, and being awake, for example. Note that various algorithms have been conventionally proposed, and any of them can be used as the specific algorithm for determination, and therefore detailed description thereof is not included here.

<Notification Control>

The receiving terminal 1r executes notification control in which the method of performing notification is changed based on the importance level set for the received information and the sleeping state of the recipient 3r. This is because consideration is given to both the desire of the sender 3s and the state of the recipient 3r.

Figure 4:
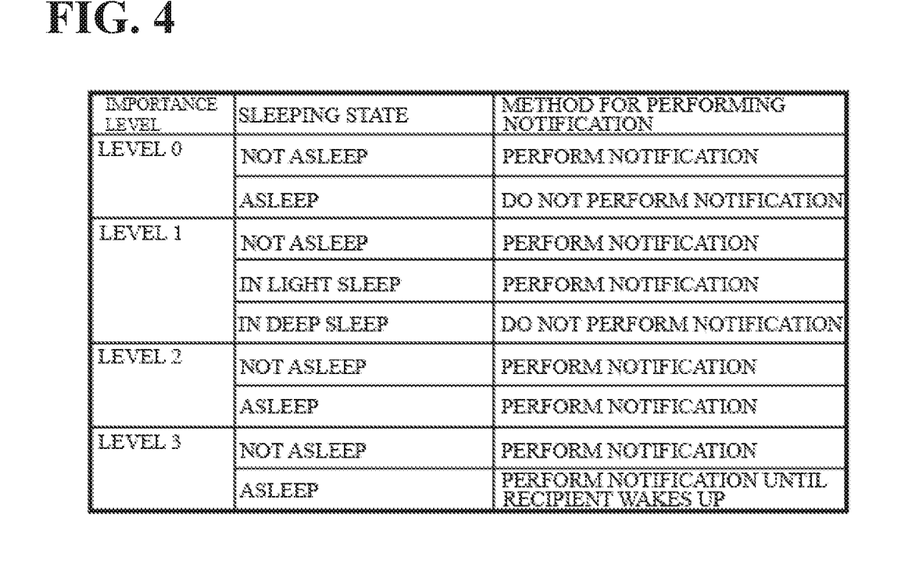
FIG. 4 is an example of a table for determining a notification control rule.

FIG. 4 is an example of a table for determining a notification control rule in the present embodiment, and correspondence relationships between the importance level, the sleeping state, and the method for performing notification are defined therein. In this example, in the case where the importance level is level 0 (lowest), notification is performed if the recipient 3r is not asleep, and notification is not performed if the recipient 3r is asleep (regardless of the depth of sleep). In the case where the importance level is 1 (low), notification is performed if the recipient 3r is not asleep or is in light sleep, and notification is not performed is the recipient 3r is in deep sleep. In the case where the importance level is level 2 (high), notification is performed regardless of whether or not the recipient 3r is asleep. In the case where the importance level is level 3 (highest), normal notification is performed if the recipient 3r is not asleep, and notification is continued or repeated until the recipient 3r wakes up if the recipient 3r is asleep. As can be understood from this example, the state of the recipient 3r is given priority over the desire of the sender 3s if the importance level is low, and the desire of the sender 3s is given priority over the state of the recipient 3r if the importance level is high.

Figure 5:
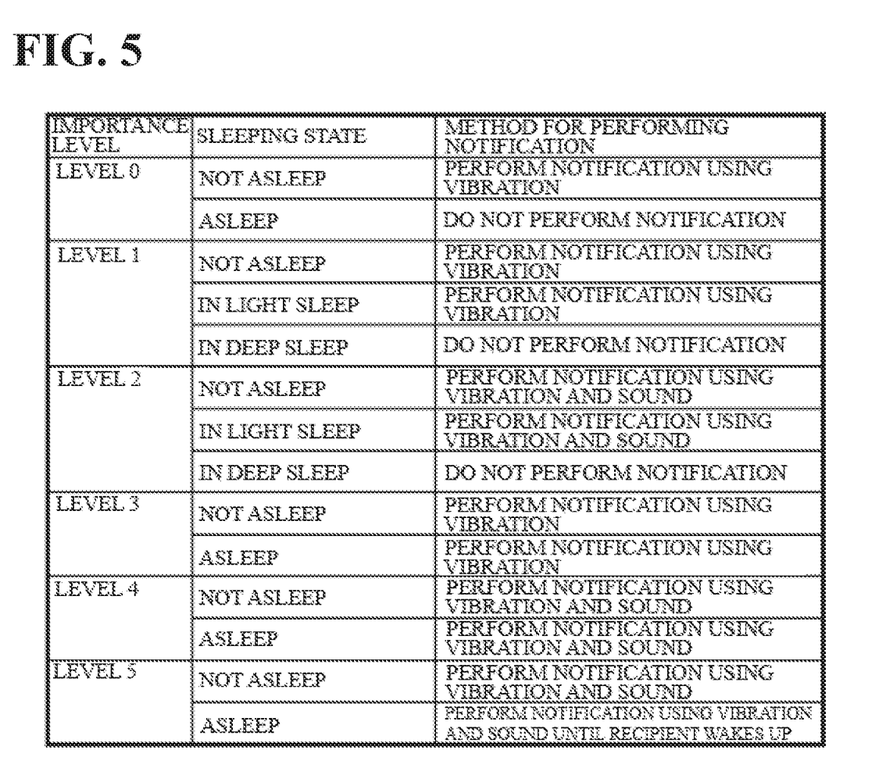
FIG. 5 is an example of a table for determining a notification control rule.

Note that the table shown in FIG. 4 is merely an example, and the correspondence relationship between the importance level, the sleeping state, and the method for performing notification may be defined in any manner. For example, with the notification control shown in FIG. 4, a switch is made between performing notification and not performing notification, but as shown in FIG. 5, it is also possible to make a switch between means of notification (performing notification using only vibration or performing notification using both vibration and sound) according to the importance level. It is also possible to change the strength of notification (volume, vibration strength, light intensity, etc.) and to change the length of notification (the amount of time for which sound or vibration continues, the number of repetitions, etc.). Furthermore, it is also possible to use a configuration in which the user (recipient 3r) can change the notification control rule defined in the table.

Figure 6:
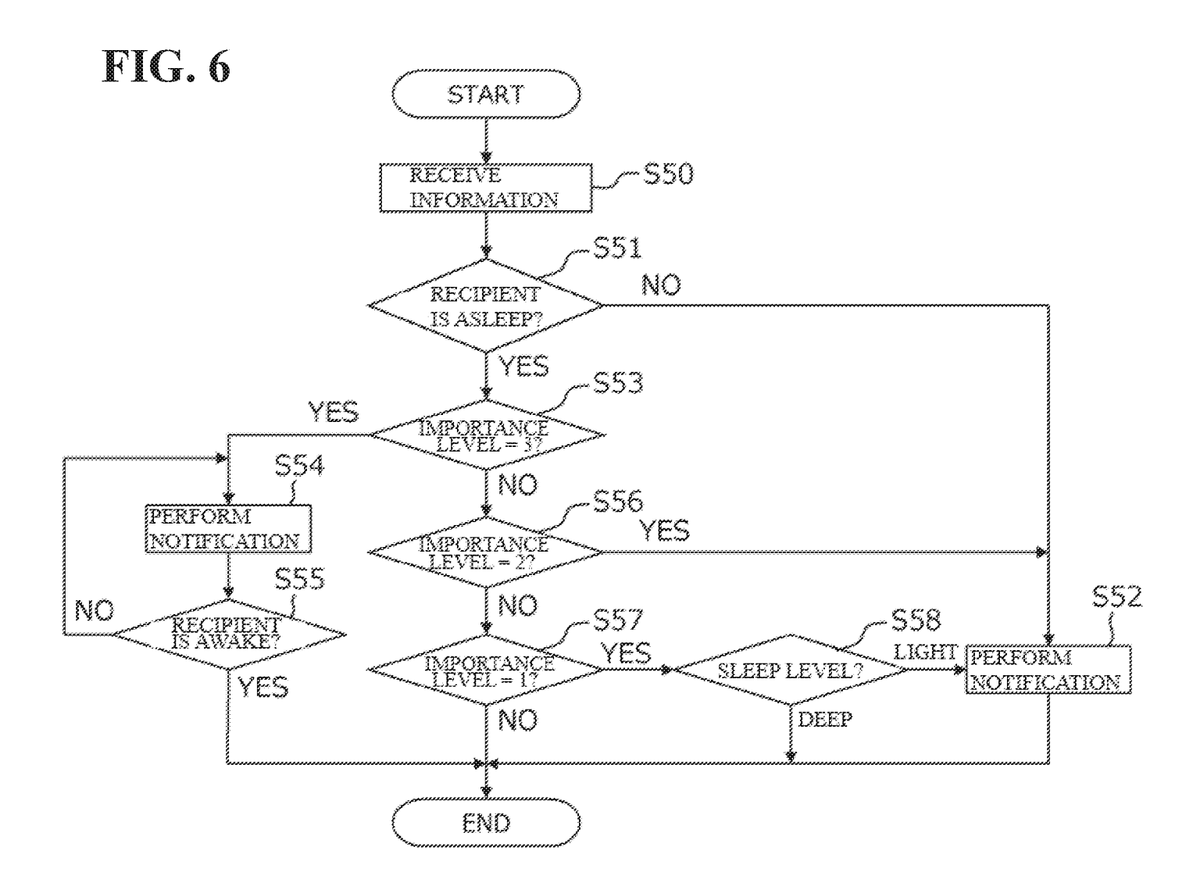
FIG. 6 is a flowchart for notification control.

The details of notification control performed by the receiving terminal 1r will be described with reference to FIG. 6. FIG. 6 is a flowchart for notification control executed when the receiving terminal 1r receives information. Note that regarding the notification control rule, the table shown in FIG. 4 is referenced.

First, the reception unit 13 receives the information addressed to the recipient 3r from the information exchange server 2 (step S50). Upon doing so, the sleeping state determination unit 14 determines the sleeping state of the recipient 3r (step S51). If the recipient 3r is not asleep (step S51: NO), the notification unit 15 uses sound, vibration, light, or the like to notify the recipient 3r that the information has been received (step S52).

On the other hand, if the recipient 3r is asleep (step S51: YES), notification control corresponding to the importance level set for the received information is executed. Specifically, if the importance level is level 3 (highest) (step S53: YES), the notification unit 15 performs notification using sound, vibration, light, or the like (step S54), and thereafter checks whether or not the recipient 3r is still asleep or is awake using the sleeping state determination unit 14 (step S55). Then, the notification unit 15 repeatedly executes notification until the recipient 3r wakes up (steps S54, S55). If the importance level is level 2 (high) (step S56: YES), the notification unit 15 performs notification using sound, vibration, light, or the like (step S52). If the importance level is level 1 (low) (step S57: YES), the notification unit 15 checks whether the sleep level of the recipient 3r is deep or light (step S58), and notification is performed only if the sleep level is light (step S52). In the case where the importance level is level 0 (lowest) and in the case where no importance level is set for the received information (step S57: NO), the notification unit 15 ends the processing without performing notification (i.e., if no importance level is set, the importance level is regarded as being level 0 (lowest)).

<Advantage of the Present Embodiment>

According to the configuration of the above-described embodiment, the method of performing notification is changed based on the "importance level of the information" set by the sender 3s and the "sleeping state" of the recipient 3r, and therefore it is possible to perform flexible notification control with consideration given to the desire of the sender of information and to the state of the recipient of the information. For example, in the case of sending information that is of low urgency and may be checked after waking up, the sender 3s sets the importance level of level 0 (lowest), whereby it is possible to perform information transmission with consideration given to the sleeping state of the recipient 3r. Also, in the case of sending information that is not very urgent but that the sender 3s wants checked soon if possible, the sender 3s sets the importance level of level 1 (low), whereby it is possible to perform information transmission with consideration given to the depth of sleep of the recipient 3r. Also, in the case of sending information that is urgent and that the sender 3s wants checked soon, the sender 3s need only perform information transmission with the importance level of level 2 (high) set. Also, in the case of sending information that is extremely urgent, the sender 3s sets the importance level of level 3 (highest), whereby it is possible to reliably convey to the recipient 3r that the information has been received.

Note that the configuration of the above-described embodiment merely illustrates a specific example of the present invention and is not intended to limit the scope of the present invention. The present invention can employ various specific configurations without departing from the technical idea of the present invention. For example, the functional configuration of the terminal, the definitions in the table, and the flow of notification control shown in the above-described embodiment are merely examples, and there is no limitation thereto, as long as the aim of the present invention can be achieved. Also, in the case where notification is continued or repeated until the recipient 3r wakes up as stated in steps S54 and S55 in FIG. 6, it is also possible to gradually increase the strength of notification and to change the pattern of the sound or vibration.

In the above-described embodiment, the importance level was selected from among levels 0 (lowest), 1 (low), 2 (high), and 3 (highest), but there is a possibility that the importance level will not be set appropriately if the sender 3s does not know the correspondence between the importance level and the notification control executed by the receiving terminal 1r. In view of this, for example, when the sender 3s selects the importance level, presses the transmit button, or the like on the user interface shown in FIG. 3, the content of the notification control corresponding to the set importance level may be presented as a pop-up or the like reading "Notification will not be performed if the recipient is sleeping", or the like. Alternatively, instead of setting the importance level using a numerical value or a level, it is also possible to allow the sender 3s to select the desired importance level from among choices stating the content of the notification control, such as "do not perform notification during sleep", "perform notification if sleep is light", and "perform notification immediately". Also, if each recipient 3r can customize the correspondence relationship between the importance level and the notification control (setting tables shown in FIGS. 4 and 5), it is preferable that the setting table of each recipient 3r can be acquired and viewed on the transmitting terminal 1s. With this kind of mechanism, the sender 3s can easily keep track of what kind of notification control will be executed by the receiving terminal 1r, and therefore the convenience for the sender 3s is improved.

The present invention may provide an information communication terminal according to the present invention is an information communication terminal including: a sleeping state determination unit configured to determine a sleeping state of a user; a reception unit configured to receive information transmitted to the user from a terminal of a sender; and a notification unit configured to notify the user that the information has been received by the reception unit, wherein the reception unit receives the information and an importance level set for the information by the sender, and the notification unit changes a method for performing notification based on the importance level set for the information and the sleeping state of the user determined by the sleeping state determination unit.

According to this configuration, the method of performing notification is changed based on the "importance level of the information" set by the sender and the "sleeping state" of the recipient (user), and therefore it is possible to perform flexible notification control with consideration given to the desire of the sender of information and to the state of the recipient of the information.

It is preferable to use a configuration in which in a case where the importance level for the information is the lowest level, the notification unit performs notification if the user is not asleep, and does not perform notification if the user is asleep. According to this configuration, when the sender sets the importance level of the information to the lowest importance level, the sleep of the recipient (user) is given priority over the notification of information reception. For example, in the case of sending information that is of low urgency and may be checked after the recipient wakes up, the sender need only select the importance level setting of the lowest level. Accordingly, the sender can perform information transmission with consideration given to the sleeping state of the recipient (user).

It is preferable to use a configuration in which the sleeping state determination unit can determine whether the sleep of the user is light or deep, and in a case where the importance level for the information is a first level, the notification unit performs notification if the user is not asleep or is in light sleep, and does not perform notification if the user is in deep sleep. According to this configuration, when the sender sets the importance level of the information to the first level, if the sleep of the recipient (user) is deep, the sleep of the recipient (user) is given priority over the notification of information reception. For example, in the case of sending information that is not very urgent but the sender wants checked soon, the sender need only select the importance level setting of the first level. Accordingly, the sender can perform information transmission with consideration given to the sleeping state, and in particular, to the depth of sleep, of the recipient (user).

It is preferable to use a configuration in which in a case where the importance level for the information is a second level that is higher than the first level, the notification unit performs notification regardless of whether or not the user is asleep. According to this configuration, when the sender sets the importance level of the information to the second level, the notification of information reception is given priority over the sleep of the recipient (user). For example, in the case of sending information that is urgent and the sender wants checked soon, it is sufficient that the sender selects the importance level setting of the second level.

It is preferable to use a configuration in which in a case where the importance level for the information is a third level that is higher than the second level, the notification unit performs notification if the user is not asleep, and continues or repeats notification until the user wakes up if the user is asleep. In the case of sending very urgent information, the sender selects the importance level setting of the third level, and thus it is possible to reliably convey to the recipient (user) that the information has been received.

It is preferable to use a configuration in which if the importance level for the information is the highest level and if the user is asleep, the notification unit continues or repeats notification until the user wakes up. In the case of sending very urgent information, the sender selects the importance level setting of the highest level, and thus it is possible to reliably convey to the recipient (user) that the information has been received.

It is preferable that the information communication terminal is a wearable terminal to be worn by the user. In the case of using a wearable terminal, detection and determination of the sleeping state of the user can be achieved relatively easily. Also, since the wearable terminal is often worn during sleep, by performing notification control with consideration given to the above-described sleeping state and depth of sleep, it is possible to prevent the sleep of the user from being needlessly disrupted, and it is possible to improve the usability of the wearable terminal.

Note that the present invention can be obtained as an information communication terminal having at least a portion of the above-described configurations or functions. Also, the present invention can be obtained as a notification apparatus built into an information communication terminal. Also, the present invention can be obtained as an information communication system including a terminal of a sender and an information communication terminal of a recipient (user). Also, the present invention can be obtained as a notification control method or information communication method including at least a portion of the above-described processing, a program for causing a computer to execute such a method, or a computer-readable storage medium permanently storing such a program. The present invention can be constituted by combining the above-described configurations and processing, as long as no technical contradiction occurs.

According to the above configuration, it is possible to realize notification control with consideration given to the desire of a sender of information and to a state of a recipient of information.

What is claimed is:

1. An information communication terminal comprising:
a device configured to output at least one of the set of: sound, light, and vibrations;
a processor; and
a memory storing a program which, when executed by the processor, causes the information communication terminal to function as:
a sleeping state determination unit configured to determine a sleeping state of a user based on measurement data by a sensor;
a reception unit configured to receive information transmitted to the user from a terminal of a sender; and
a notification unit configured to control the device to notify the user that the information has been received by the reception unit,
wherein the reception unit receives the information and an importance level set for the information by the sender, and
the notification unit controls the device so as to change a method for performing notification based on the importance level set for the information and the sleeping state of the user determined by the sleeping state determination unit by referring to a table which defines a correspondence relationship between the importance level, the sleeping state, and the method for performing notification.

2. The information communication terminal according to claim 1,
wherein in a case where the importance level for the information is the lowest level, the notification unit performs notification if the user is not asleep, and does not perform notification if the user is asleep.

3. The information communication terminal according to claim 1,
wherein the sleeping state determination unit is configured to determine whether the sleep of the user is light or deep based on the measurement data, and
in a case where the importance level for the information is a first level, the notification unit performs notification if the user is not asleep or is in light sleep, and does not perform notification if the user is in deep sleep.

4. The information communication terminal according to claim 3,
wherein in a case where the importance level for the information is a second level that is higher than the first level, the notification unit performs notification regardless of whether or not the user is asleep.

5. The information communication terminal according to claim 4,
wherein in a case where the importance level for the information is a third level that is higher than the second level, the notification unit performs notification if the user is not asleep, and continues or repeats notification until the user wakes up if the user is asleep.

6. The information communication terminal according to claim 1,
wherein if the importance level for the information is the highest level and if the user is asleep, the notification unit continues or repeats notification until the user wakes up.

7. The information communication terminal according to claim 1,
wherein the information communication terminal is a wearable terminal configured to be worn by the user.

8. An information communication terminal comprising:
a device configured to output at least one of the set of: sound, light, and vibrations;
a processor; and
a memory storing a program which, when executed by the processor, causes the information communication terminal to function as:
a sleeping state determination unit configured to determine a sleeping state of a user based on measurement data by a sensor;
a reception unit configured to receive information transmitted to the user from a terminal of a sender; and
a notification unit configured to control the device to notify the user that the information has been received by the reception unit,
wherein the reception unit receives the information and an importance level set for the information by the sender, and
the notification unit controls the device so as to change a method for performing notification based on the importance level set for the information and the sleeping state of the user determined by the sleeping state determination unit,
wherein the importance level which the sender can set for the information includes at least:
a level for a notification control in which notification is performed in a case where the user is not asleep and is not performed in a case where the user is asleep; and
a level for a notification control in which notification is performed regardless of whether or not the user is asleep.

* * * * *